(12) United States Patent
Task et al.

(10) Patent No.: US 6,194,701 B1
(45) Date of Patent: Feb. 27, 2001

(54) PORTABLE NIGHT VISION GOGGLE HAZE AND TRANSMISSIVITY MEASUREMENT DEVICE

(75) Inventors: Harry L. Task, Dayton; Alan R. Pinkus, Bellbrook; Sheldon E. Unger, Englewood, all of OH (US)

(73) Assignee: The United States of Americas as represented by the Secretary of the Air Force, Washington, DC (US)

(*) Notice: Subject to any disclaimer, the term of this patent is extended or adjusted under 35 U.S.C. 154(b) by 0 days.

(21) Appl. No.: 09/287,078

(22) Filed: Apr. 6, 1999

(51) Int. Cl.[7] .................. G01N 21/59; G01N 21/958
(52) U.S. Cl. .................. 250/214 VT; 356/432; 356/333
(58) Field of Search .................. 250/214 VT, 216, 250/559.16, 559.17, 330, 333, 339.11, 341.8; 356/432, 433, 434, 435, 443, 445, 446, 447, 448, 337, 338

(56) References Cited

U.S. PATENT DOCUMENTS

| | | | |
|---|---|---|---|
| 4,623,258 | * 11/1986 | Task et al. | 356/432 |
| 4,687,338 | * 8/1987 | Task et al. | 356/446 |
| 4,764,007 | * 8/1988 | Task et al. | 351/243 |
| 4,946,282 | * 8/1990 | Task et al. | 356/432 |
| 5,712,709 | * 1/1998 | Task et al. | 356/432 |

\* cited by examiner

*Primary Examiner*—John R. Lee
(74) *Attorney, Agent, or Firm*—Bobby D. Scearce; Thomas L. Kundert

(57) ABSTRACT

Device and method are described for measuring transmissivity and haze in transparencies as detected through night vision goggles, including an emitter portion and a sensor portion, the emitter portion including a first light source for presenting an image to the sensor portion through the transparency and a second light source for projecting a haze producing light onto the transparency, the sensor portion including a light intensifier tube and a photometer for measuring the luminance output of the light intensifier tube and quantifying attenuation (transmissivity) and haze (light scatter) characteristics of the transparency as viewed through night vision goggles.

6 Claims, 3 Drawing Sheets

PORTABLE NIGHT VISION GOGGLE HAZE AND TRANSMISSIVITY MEASUREMENT DEVICE

RIGHTS OF THE GOVERNMENT

The invention described herein may be manufactured and used by or for the Government of the United States for all governmental purposes without the payment of any royalty.

BACKGROUND OF THE INVENTION

The present invention relates generally to devices and methods for measuring haze and transmissivity in transparencies, and more particularly to a device and method for measuring haze and transmissivity of aircraft transparencies as viewed through night vision goggles.

Night vision goggles (NVGs) are being used by aircrew members with increasing frequency during nighttime flight and ground operations. Concurrently, aircraft transparencies are constantly undergoing improvements in materials such as acrylic to polycarbonate and their surfaces are being treated with gold, indium-tin-oxide or other coatings. Ground vehicles are being equipped with bullet-resistant glass which may be fabricated using a combination of specially treated plastic and glass materials. These material changes may attenuate the infrared (IR) energy utilized by NVGs thereby degrading the visual acuity of the aircrew member. Aircrew members have informally reported lowered visual performance while using NVGs in some aircraft equipped with coated canopy systems. Traditional transmissivity and haze measurements made in the visible spectral region (400–700 nm) cannot characterize the entire problem. Preliminary laboratory measurements of sample coated canopies found that IR transmissivities of windscreen coatings varied considerably among manufacturers thereby affecting observer performance (see, Pinkus et al, "The Effects of Aircraft Transparencies on Night Vision Goggle-Mediated Visual Acuity," SAFE Symposium Proceedings (1997) pp 93–104). However, NVG-mediated visual performance through canopies is not solely affected by IR attenuation, but also by haze resulting from scatter of incident light.

The invention solves or substantially reduces in critical importance problems in the prior art by providing a portable device and method for measuring transmissivity and haze of aircraft transparencies as viewed through NVGs. The invention includes a pair of light sources for projecting a transmitted beam and a haze producing beam onto a transparency and sensor portion including a light intensifier tube of an NVG and photometer for measuring the luminance output thereof in order to quantify the NVG weighted attenuation (transmissivity) and haze (light scatter) characteristics of the transparency.

The invention finds utility for measuring the IR transmissivity and IR haze characteristics of transparencies important in selection of coating materials (gold, indium-tin-oxide) for use with NVGs, quality control of the coatings within and among transparency manufacturers, quick-response field evaluations of transparency and NVG integration issues, life-cycle costs of coatings, monitoring deleterious environmental effects (acid rain, sand abrasion, bio-chemical) on coating integrity, maintenance procedures, and visual performance of an NVG-equipped aircrew member.

It is therefore a principal object of the invention to provide system and method for measuring transmissivity and haze in a transparency.

It is a further object of the invention to provide system and method for measuring infrared transmissivity and haze in a transparency as viewed using night vision goggles.

It is another object of the invention to provide system and method for measuring the effect of using night vision goggles on the observed infrared transmissivity and haze in a transparency.

It is another object of the invention to provide a device and method for field evaluation of transparencies.

It is yet another object of the invention to provide an improved system and method for measuring transmissivity and haze in aircraft transparencies.

It is yet another object of the invention to provide a reliable portable transmissivity and haze measurement device.

These and other objects of the invention will become apparent as a detailed description of representative embodiments proceeds.

SUMMARY OF THE INVENTION

In accordance with the foregoing principles and objects of the invention, device and method are described for measuring transmissivity and haze in transparencies as detected through night vision goggles, including an emitter portion and a sensor portion, the emitter portion including a first light source for presenting an image to the sensor portion through the transparency and a second light source for projecting a haze producing light onto the transparency, the sensor portion including a light intensifier tube and a photometer for measuring the luminance output of the light intensifier tube and quantifying attenuation (transmissivity) and haze (light scatter) characteristics of the transparency as viewed through night vision goggles.

DESCRIPTION OF THE DRAWINGS

The invention will be more clearly understood from the following detailed description of representative embodiments thereof read in conjunction with the accompanying drawings wherein.

DETAILED DESCRIPTION

Figure 1:
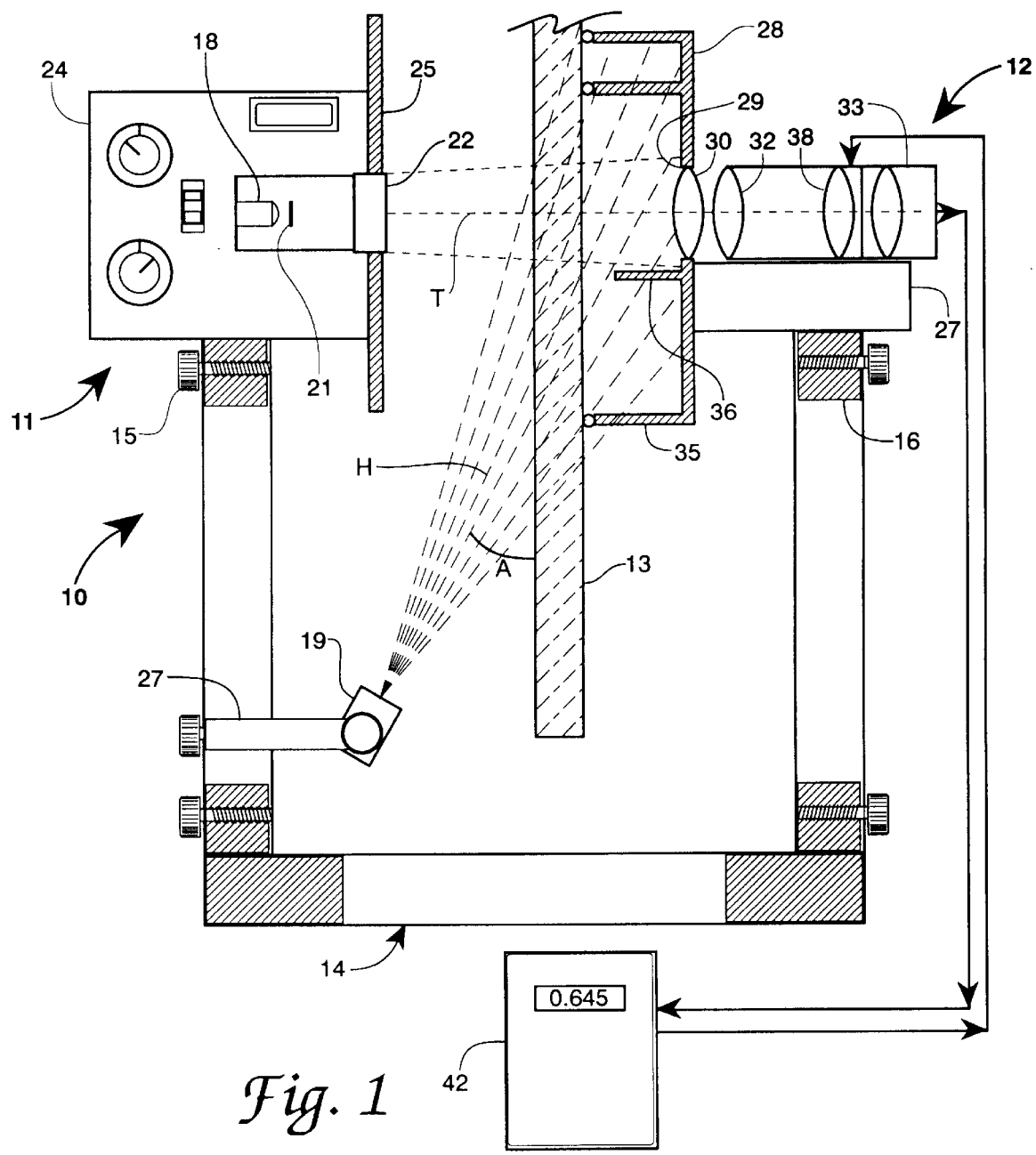
FIG. 1 shows a schematic side elevational view of a representative embodiment of the portable haze and transmissivity measurement device the invention.
Figure 2:
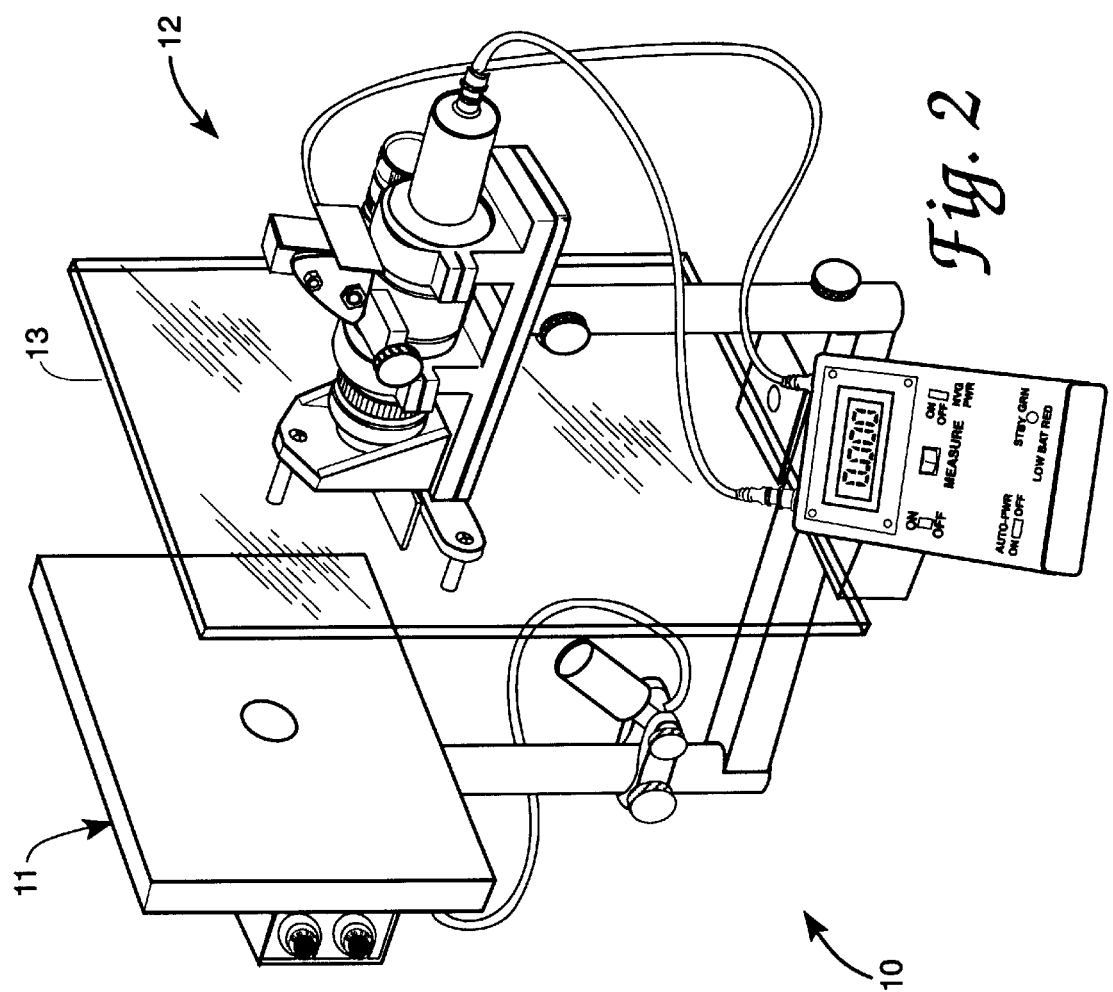
FIG. 2 shows a perspective view of the representative embodiment of the invention shown in FIG. 1 which was built in demonstration of the invention.

Referring now to the drawings, FIG. 1 shows a schematic side elevational view of a representative embodiment of the portable haze and transmissivity measurement device 10 of the invention. FIG. 2 shows a perspective view of the device 10 shown in FIG. 1 which was built in demonstration of the invention. Device 10 principally comprises two system portions including an emitter portion 11 and a sensor portion 12. Emitter portion 11 and sensor portion 12 are configured to be supported in a confronting arrangement on opposite sides of a transparency 13 under examination utilizing any suitable support structure such as the U-bracket structure 14 upon which portions 11,12 may be independently adjustably mounted using means such as suggested in FIG. 1 as assembly screw brackets 15,16 adjustably mounted on U-bracket structure 14. U-bracket structure 14 may preferably be configured to support and position emitter portion 11 and sensor portion 12 around an aircraft transparency edge while maintaining suitable respective pre-calibrated positions of emitter portion 11 and sensor portion 12.

Emitter portion 11 includes a first light source 18 for presenting an image thereof to sensor portion 12 along a first optical axis T through transparency 13, and a second source 19 providing an infrared haze illuminator beam directed onto transparency 13 along a second optical axis H disposed at a preselected angle A to transparency 13. Any suitable near-infrared producing type light source may be used for sources 18,19 as would occur to the skilled artisan practicing the invention in accordance with these teachings, such as light emitting diodes (LEDs) or miniature incandescent lamps. In the device depicted in the FIGS. 1,2, and built in demonstration of the invention, LEDs were used because of their desirable spectral characteristics and characteristic stability, ruggedness, low electrical consumption and small size. The outputs of sources 18,19 were controlled by circuitry described below in relation to FIG. 3. A diffuser baffle 21 and translucent diffuser 22 may be placed along optical axis T in order to provide a suitably diffuse light surface image presented to sensor portion 12 along axis T. A suitable light tight housing 24 with protective mask 25 disposed at one wall thereof prevents stray light from interfering with the generation and projection of the desired diffuse image along axis T in the measurement of the transmissivity of transparency 13 as described in detail below. Second light source 19 (also an LED in the demonstration unit) is positioned in a spaced relationship a predetermined distance from light source 18 such as attached to a leg of U-bracket structure 14 by a bracket and position locking knob assembly 26 as suggested in FIGS. 1,2. Source 18 is disposed for projecting a haze illuminator beam at an angle over the portion of transparency 13 under inspection, directly onto the transparency so that the unscattered light therefrom does not project directly into sensor portion 12 of device 10 for reasons discussed more fully below. Sources 18,19 each may be surrounded by suitable foam masks to prevent damage to the surface of transparency 13 under inspection.

Sensor portion 12 includes a support means such as bracket and positioning knob assembly 27 adjustably attached to a leg of U-bracket structure 14 as suggested in FIG. 1. Assembly 27 supports tripod transparency positioner 28 providing precision three-point alignment of transparency 13 with respect to the path of the transmisssivity light beam projected along optical axis T. Within central aperture 29 in positioner 28 is disposed focusing lens 30 for collimating light transmitted through transparency 13 along axis T into the objective lens 32 of one ocular (viz, a light intensifer tube) 33 of an NVG disposed along axis T. The use of an NVG as the initial sensor of the device provides the necessary sensitivity and spectral weighting for measurements that relate to NVG-mediated visual performance of transparency 13.

The structure and operation of various types of image intensifier tubes may be found by reference to Illes P. Csorba, *Image Tubes* (Howard W. Sams & Co. Inc., Indianapolis, 1985). The types of image intensifier tubes which may be included in the structure of sensor portion 12 may include a third generation NVG (GEN-III) or a second generation NVG (GEN-II) (for operation at about 0.3 to 0.9 $\mu$m), or InGaAs (for operation at about 0.3 to 1.0 $\mu$m), or other type occurring to the skilled artisan guided by these teachings. Operation of an image intensifier tube may be generally described as electronically amplifying an image illuminated by a low level of lighting, such as that which characterizes nighttime light or illuminated by light in regions of the electromagnetic spectrum to which the human eye is not sensitive, viz., the NIR and UV regions of the spectrum. (General discussions of the structure and operation of NVGs may be found by reference to Thomas J. Tredici et al, *Night Vision Manual for the Flight Surgeon*, USAFSAM-TR-85-3 (1985), or to F. Baratte et al, "Night Vision Tubes and Solid-State Devices," Special Electronics (1984), 36–41). An intensifier tube is a high vacuum tube comprising three basic components, viz., a photocathode disposed on a fiberoptic faceplate, a microchannel plate and a phosphor screen disposed axially along the viewing axis of the tube. The photocathode converts photons of light from a low-level light image into electrons. The microchannel plate comprises a multiplicity of coaxially disposed optical channels in which the electrons from the photocathode are amplified. The phosphor screen converts the electrons from the microchannel plate into a visible image. The tube may further include a fiber optic twist supporting the phosphor screen for inverting the visible image, a focusable objective lens, an eyepiece lens for magnifying the image, and a battery pack for providing power to the photocathode and the microchannel plate.

The three prongs 35 of tripod positioner 28 define the plane of transparency 13 with respect to axis T during a haze/transmissivity measurement using device 10, and, accordingly, the ends of each prong 35 contacting transparency 13 may preferably be tipped with soft plastic or other resilient material to prevent damage to the contacted surface of transparency 13. Light baffle 36 is disposed on tripod positioner 28 near aperture 29 in order to block projection of light from light source 19 through transparency 13 directly onto focusing lens 30.

Preparatory to obtaining measurements of haze/transmissivity on transparency 13 utilizing device 10, objective lens 32 and eyepiece lens 38 of ocular 33 are prefocused to optical infinity before placement onto bracket assembly 27 in optical alignment with focusing lens 30. Focusing lens 30 is disposed one focal length (of lens 30) away from diffuser 22 in order to produce an image of diffuser 22 at infinity that will be in focus to NVG ocular 33. The luminance output of ocular 33 may be measured utilizing suitable liminance tester (photometer) 42 known in the art, such as that described in U.S. Pat. No. 5,070,239 to Pinkus (Dec. 3, 1991), the entire teachings of which are incorporated by reference herein. Measurements are preferably performed in a darkened room or, for field measurements, at a substantially dark outside location at night free of extraneous lights. Ocular 33 and tester 42 are preferably turned on and allowed to stabilize for a few minutes before making measurements.

Figure 3:
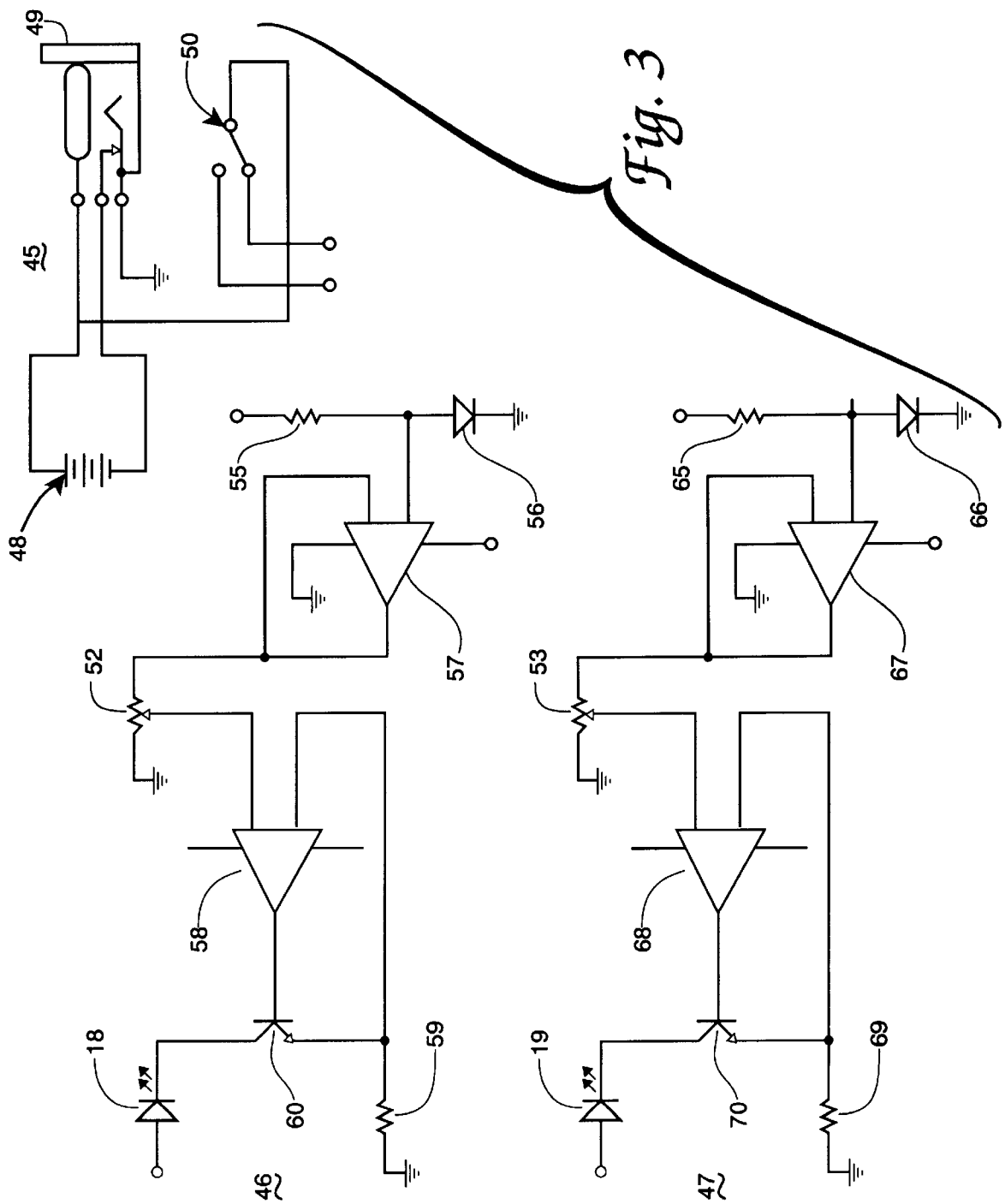
FIG. 3 shows a representative electronic control circuit for the device shown in FIG. 1.

Referring now to FIG. 3 shown therein are representative electronic control circuits 45,46,47 defining, respectively, a power circuit and control circuits for light sources 18,19 for device 10 of FIGS. 1,2. Device 10 may be powered by battery pack 48 for substantial portability of the system or by DC input 49. Three position power switch 50 provides means for selectively directing power to circuit 46 of light source 18 or to circuit 47 of light source 19. Potentiometer 52 allows adjustment of the current level through (transmittance) light source 18 and potentiometer 53 allows adjustment of the current level through (haze) light source 19. In circuit 46, the resister 55, diode 56, operational amplifier 57 combination provides a constant voltage source to potentiometer 52 which controls the voltage level applied to second operational amplifier 58. Current sensing resistor 59 provides feedback to amplifier 58, which maintains a constant current level through transistor 60 and light source 18. Likewise, in circuit 47, the resister 65, diode 66, operational amplifier 67 combination provides a constant voltage source to potentiometer 53 which controls the voltage level applied to second operational amplifier 68. Current sensing resistor 69 provides feedback to amplifier 68, which maintains a constant current level through transistor 70 and light source 19

The IR transrnissivity measurement using source 18 characterizes the NVG-weighted light attenuation qualities of a transparent part, such as transparency 13, and the IR haze measurement using source 19 characterizes the NVG-weighted light scattering qualities of a transparent part (see, Task et al, U.S. Pat. No. 4,687,338, *Method of Measurement of Haze in Transparencies* (Aug. 18, 1987); Task et al, U.S. Pat. No. 4,623,258, *Method for Measuring Haze in Transparencies*. (Nov. 18, 1986); Task, U.S. Pat. No. 4,946,282, *Transparency Transmissivity Measurement Device* (Aug. 7, 1990); Task et al, U.S. Pat. No. 5,712,709, *Haze and Transmissivity Measurements* (Jan. 27, 1998); ASTM F 943-90 (Standard Test Method for Measuring Halation [haze] of Transparent Parts), ASTM F 1316-90 (Standard Test Method for Measuring the Transmissivity of Transparent Parts), ASTM D 1003-61 (Standard Test Method for Haze and Luminous Transmittance of Transparent Parts), and ASTM 1863-98 (Night Vision Goggle Compatibility of Transparent Materials), *Annual Book of American Society for Testing and Materials*, 15.03; and Pinkus et al, Interlaboratory Study (ILS) of the Standard Test Method for Measuring Night Vision Goggle-Weighted Transmissivity of Transparent Parts, Tech Report AFRL-HE-WP-TR-1998-0016, Wright-Patterson AFB OH (1998)).

For an IR transmissivity measurement, source 18 is energized. Potentiometer 52 can be adjusted until the NVG luminance output 41, as measured by tester 42, reads 1.00. Device 10 is then placed around transparency 13 with tripod positioner 28 pressed against the transparency 13 surface area to be measured (FIG. 2). A second tester 42 reading is then recorded. When the baseline is set to exactly 1.00 fL, the resultant reading is the IR transmissivity, no calculation required. IR transmissivity is calculated by taking the measurement through transparency 13 and dividing by the baseline value (either 1.00 or another measured value).

For an IR haze measurement, source 19 is energized. Optical axis H is positioned using the source 19 support bracket at an acute angle relative to focusing lens 30 of sensor portion 12. This acute angle, when used in conjunction with light baffle 36, assures that light from source 19 does not shine directly into lens 30. A baseline measurement is taken to verify that no light from source 19 is entering sensor portion 12 and if there is any ambient IR pollution present that needs to be accounted for in the haze calculation. When a transparent part 13 is placed against tripod positioner 28, its imperfections scatter light creating haze. Some of the scattered light can then shine into sensor portion 12 to be amplified and measured as described above.

The entire teachings of all references cited herein are incorporated herein by reference.

The invention therefore provides to a portable, light weight, self-contained, device for field transmissivity and haze measurements on transparencies of substantially any shape, such as aircraft canopies. It is understood that modifications to the invention may be made as might occur to one with skill in the field of the invention within the scope of the appended claims. All embodiments contemplated hereunder that achieve the objects of the invention have therefore not been shown in complete detail. Other embodiments may be developed without departing from the spirit of the invention or from the scope of the appended claims.

We claim:

1. A device for measuring transmissivity and haze in transparencies as detected through night vision goggles, comprising:

(a) an emitter portion for placement near a first side of a transparency and a sensor portion for placement near the second side of the transparency in substantial confronting relationship with said emitter portion;

(b) said emitter portion including a first infrared producing light source for presenting an image thereof to said sensor portion along a first optical axis through the transparency, and a second infrared producing light source disposed in preselected spaced relationship from said first light source for projecting light along a second optical axis disposed at a preselected angle to the first side of the transparency for producing haze in the transparency;

(c) said sensor portion including a focusing lens disposed along said first optical axis for focusing light transmitted through the transparency, a light intensifier tube, and a photometer operatively connected to said light intensifier tube for measuring the luminance output thereof; and (d) a source of power for said emitter and sensor portions.

2. The device of claim 1 wherein said first and second light sources comprise light emitting diodes or incandescent lamps.

3. The device of claim 1 further comprising a light baffle disposed near said focusing lens of said sensor portion for blocking direct light transmission from said second source to said focusing lens.

4. The device of claim 1 wherein said emitter portion further comprises a translucent diffuser disposed along said first optical axis for presenting a diffuse surface image to said sensor portion along said first optical axis.

5. The device of claim 4 further comprising a substantially light tight housing enclosing said first light source, said housing having said diffuser disposed in one wall thereof.

6. The device of claim 4 wherein said focusing lens is disposed one focal length thereof from said diffuser whereby an image of said diffuser is produced that is in focus at said image intensifier tube.

* * * * *